US00PP18771P2

(12) United States Plant Patent
Bradford

(10) Patent No.: US PP18,771 P2
(45) Date of Patent: Apr. 29, 2008

(54) PEACH TREE NAMED 'MAY PRINCESS'

(50) Latin Name: *Prunus persica*
Varietal Denomination: May Princess

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,906

(22) Filed: Dec. 13, 2006

(51) Int. Cl.
*A01H 5/00* (2006.01)

(52) U.S. Cl. ..... Plt./197
(58) Field of Classification Search ..... Plt./197
See application file for complete search history.

(56) References Cited

U.S. PATENT DOCUMENTS

PP7,070 P * 12/1989 Bradford et al.

* cited by examiner

*Primary Examiner*—Kent Bell

(57) ABSTRACT

The present invention relates to a new and distinct variety of peach tree, *Prunus persica,* broadly characterized by a large size, vigorous, hardy, self-fertile, productive and regular bearing tree. The fruit matures under the ecological conditions described in mid May, with the first picking on May 19, 2006. The fruit is uniformly medium in size, acidic and sweet in flavor, oblate in shape, clingstone in type, firm and non-melting in texture, yellow in flesh color, and red mottled over yellow in skin color.

1 Drawing Sheet

Botanical classification: *Prunus persica.*
Variety denomination: 'MAY PRINCESS'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'MAY PRINCESS'.

During the spring of 1998 I gathered fruit from several different unnamed seedlings in my experimental orchard located near Le Grand, Calif., in Merced County (San Joaquin Valley). One particular group of peaches was early in maturing, yellow in flesh color, and clingstone in type, and was designated "VEP (OP)". I used embryo rescue techniques to germinate the seeds from this fruit, grew them as seedlings on their own root in my greenhouse, and upon reaching dormancy transplanted them to a cultivated area in the experimental orchard described above. During the fruit evaluation season of 2000 I selected the claimed variety as a single tree from this group of "VEP (OP)" described above. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is most similar to 'Crown Princess' (U.S. Plant Pat. No. 7,070) peach by producing peaches that are very firm and non-melting in texture, yellow in flesh color, and a red primary skin color, but is distinguished therefrom by requiring much less chilling hours, by having a sweet instead of bitter kernel, by having reniform instead of globose leaf glands, and by producing fruit that is smaller in size, that is flatter in shape, that has a light yellow background skin color, and that matures about three weeks earlier.

SUMMARY OF VARIETY

In summary, the present variety is characterized by a large size, vigorous, hardy, self-fertile, productive and regular bearing tree. The fruit matures under the ecological conditions described in the early part of May, with first picking on May 19, 2006. The fruit is uniformly medium in size, mildly acidic and sweet in flavor, oblate in shape, clingstone in type, firm and non-melting in texture, yellow in flesh color, and red mottled over yellow in skin color.

DRAWING

The accompanying photograph consists of four whole fruits positioned to display the characteristics of the skin color and form, one fruit divided transversely to the suture plane to reveal the flesh and stone, two insets to reveal blossoms and buds in various stages, two leaves, and a typical tip shoot.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on May 21, 2006, on the original tree during its eighth growing season. All major color code designations are by reference to the Inter-Society Color Council, National Bureau of Standards. Common color names are also used occasionally.

Tree

Size: Large, reaching and maintaining a height of 11' [3.35 m.] and a spread of 10' [3.05 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 350 hours.

Trunk:

*Size.*—Medium, reaching a maximum diameter of 5¾" [146 mm.] after the eighth growing season.

*Texture.*—Shaggy.

*Bark color.*—A Grayish brownish [61. gy.Br] and Moderate reddish brown [43. m.rBr] variegation.

*Lenticels.*—Approximate Number Per Square Inch: 4. Color: Light yellowish brown [76. l.yBr]. Typical Size: ⅛" [3.2 mm.] to 7/16" [11.1 mm.]. Shape: Eye-shaped to elongated.

Branches:

*Size.*—Diameter of limb is 3¾" [95 mm.] measured 12" above the crotch, 2⅜" [60 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Number Per Square Inch: More than 60 on second year wood. Color: Light yellowish brown [76. l.yBr]. Typical size: 1/64" [0.4 mm.] to ⅛ [3.2 mm.]. on second year wood. Shape: Elongated.

Leaves:

*Size.*—Large. Average Length: 6" [152 mm.]. Average width: 1¼" [32 mm.].

*Arrangement.*—Alternate.

*Thickness.*—Medium.

*Form.*—Elliptical.

*Apex.*—Acuminate.

*Base.*—Acute with a base angle of 70 to 80 degrees.

*Surface.*—Smooth.

*Color.*—Dorsal Surface: Moderate olive green [125. m.OlG]. Ventral Surface: Deep yellow green [118. deep YG].

*Margin.*—Finely serrate.

*Venation.*—Pinnately net veined.

*Petiole.*—Average Length: ⅜" [9.5 mm.]. Average Thickness: 1/16" [1.6 mm.]. Color: Strong yellow green [117. s.YG].

*Stipules.*—Number: Usually 2 per leaf, up to 6 per growing tip. Average Length: ¼" [6.4 mm.]. Color: Very yellow green [115. v.YG] becoming Strong brown [55. s.Br] with age.

*Glands.*—Number: 2 to 4. Position: Mostly alternate, positioned on the petiole and base of leaf blade. Size: Medium. Form: Reniform. Color: Strong yellow green [117. s.YG] becoming Moderate reddish brown [43. m.rBr] with age.

*Leaf buds.*—Very large, pointed.

Flower buds:

*Hardiness.*—Hardy, with respect to central California winters.

*Diameter.*—Typically ⅜" [9.5 mm.] 1 week before bloom.

*Length.*—Typically 9/16" [14.3 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepal and petal locations alternately positioned.

*Type.*—Showy, large.

*Average flower diameter.*—1⅞" [47.6 mm.].

*Number of petals.*—Usually five, with double blossoms and extra petal fragments rare.

*Petal shape.*—Circular to oval.

*Petal margin.*—Somewhat wavy.

*Average petal diameter.*—11/16" [17.5 mm.].

*Average petal length.*—¾" [19.1 mm.].

*Petal apex.*—Rounded.

*Petal base.*—Rounded to somewhat truncate.

*Petal color.*—Pale pink [7. p.Pk] toward the apex, Light pink [4. l.Pk] toward the base.

*Anther color.*—Dark red [16. d.R] over a Light yellow [86. l.Y] center at bloom onset.

*Stigma color.*—Light greenish yellow [101. l.gY].

*Sepal color.*—Dark purplish red [259. d.pR].

*Sepal length.*—¼" [6.4 mm.].

*Sepal width.*—3/16" [4.8 mm.].

*Average pistil length.*—¾" [19.1 mm.].

*Average stamen length.*—⅝" [15.9 mm.].

*Fragrance.*—Moderate.

*Blooming period.*—Very early, fourteen days before 'Rose Diamond' (U.S. Plant Pat. No. 7,421) nectarine.

*Onset of bloom.*—One percent on Feb. 5, 2006.

*Date of full bloom.*—Feb. 15, 2006.

*Duration of bloom.*—One to two weeks, dependent on ambient temperature.

*Number per cluster.*—1 to 3 with single flowers most common.

FRUIT

Maturity when described: Firm ripe, May 21, 2006.

Date of first picking: May 19, 2006.

Date of last picking: May 27, 2006.

Size: Uniform, medium.

*Average diameter axially.*—2⅝" [66.7 mm.].

*Average diameter across cheek plane.*—2⅞" [73.0 mm.].

*Average diameter across suture plane.*—2⅞" [73.0 mm.].

*Typical weight.*—5.9 ounces [167 grams].

Form: Uniform, oblate, symmetrical.

*Longitudinal section form.*—Oblate to elliptical.

*Axial view.*—Round.

Suture: Sharp groove in the stem cavity, a very shallow trough along the side, and a shallow groove toward the apex ending just beyond the pistil point in a moderate depression.
Ventral surface: Rounded, slightly lipped toward the apex.
Lips: Equal.
Cavity: Flaring, rounded, suture showing on one side, Light Yellow [86. l.Y] stem markings typical.
*Depth.*—⅜" [9.5 mm.].
*Breadth.*—1" [25.4 mm.].
Base: Truncate, somewhat cordate if viewed parallel to the suture.
Apex: Truncate, slightly cordate if viewed parallel to the suture.
Pistil point: Oblique, negligible in length, usually depressed within the suture.
Stem: Medium.
*Average length.*—⅜" [9.5 mm.].
*Average width.*—3/16" [4.8 mm.].
Skin:
*Thickness.*—Medium.
*Surface.*—Medium.
*Tenacity.*—Tenacious to flesh.
*Astringency.*—Somewhat astringent.
*Tendency to crack.*—Minimal.
*Color.*—Dark red [16. d.R] mottled with Moderate reddish orange [37. m.rO] over a Light yellow [86. l.Y] background.
Down: Moderate to scant, short, does not roll up when rubbed.
Flesh:
*Color.*—Light Yellow [86. l.Y] from the stone to the skin, but will acquire a slight amount of Very red [11. v.R] flecking toward the skin with further maturity.
*Surface of pit cavity.*—Pale yellow [89. p.Y] broken fibers when twisted away from the stone.
*Amygdalin.*—Moderate.
*Juice.*—Abundant, rich.
*Texture.*—Firm, non-melting.
*Fibers.*—Abundant, fine.
*Ripens.*—Slightly earlier at the apex.
*Flavor.*—Acidic and sweet, 12 to 15 brix.
*Aroma.*—Moderate.
*Eating quality.*—Very good.

STONE

Type: Clingstone.
Form: Oval.
Hilum: Narrow, oval.
Base: Straight.
Apex: Acute with a ⅛" [3.2 mm.] tip.
Sides: Equal.
Surface: Irregularly furrowed toward the apex and along the ventral edge, pitted toward the base.
Ridges: Jagged.
External color: Light yellowish brown [76. l.yBr].
Internal color when cracked: Light orange yellow [70. l.OY].
Cavity surface color: Light yellowish brown [76. l.yBr] with Deep yellowish brown [75. deep yBr] blotching.
Average pit wall thickness: ¼" [6.4 mm.].
Average width: ¾" [19.1 mm.].
Average length. 1" [25.4 mm.].
Average breadth: 9/16" [14.3 mm.].
Tendency to split: Slight.
Kernel:
*Form.*—Oval.
*Skin color.*—Light yellowish brown [76. l.yBr] when dried.
*Pellicle color.*—Moderate yellowish brown [77. m.yBr].
*Vein color.*—Moderate yellowish brown [77. m.yBr].
*Taste.*—Sweet.
*Viable.*—Only by using embryo rescue techniques.
*Average width.*—⅜" [9.5 mm.].
*Average length.*—⅝" [15.9 mm.].
*Amygdalin.*—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar 'Crown Princess' (U.S. Plant Pat. No. 7,070) peach by producing peaches that are very firm and non-melting in texture, yellow in flesh color, and red in primary skin color, but is distinguished therefrom by requiring much less chilling hours, by having a sweet instead of bitter kernel, by having reniform instead of globose leaf glands, and by producing fruit that is smaller in size, that is flatter in shape, that has a light yellow background skin color, and that matures about three weeks earlier.

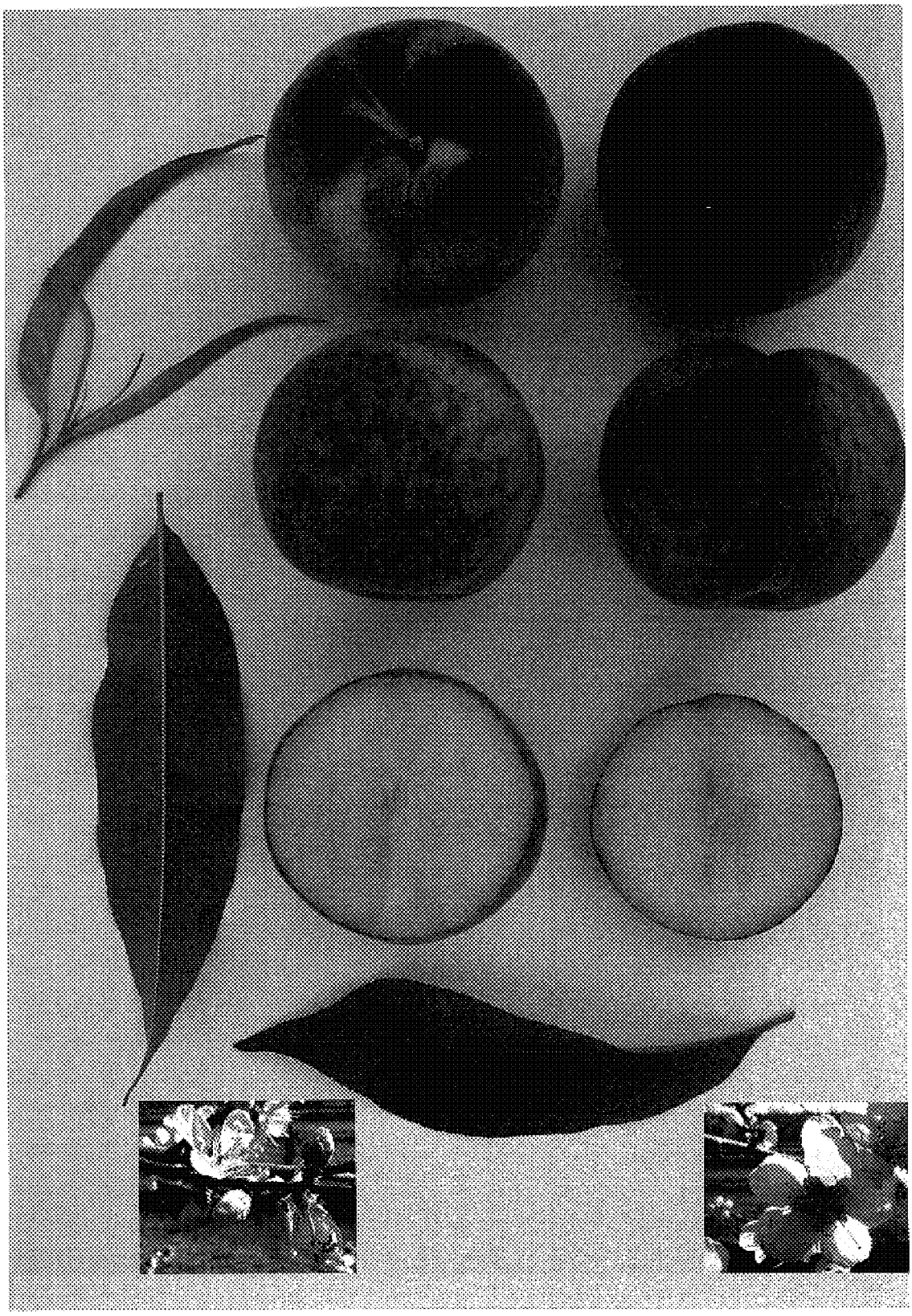

* * * * *